United States Patent [19]

Marshall et al.

[11] Patent Number: 5,040,112
[45] Date of Patent: Aug. 13, 1991

[54] METHOD OF SEPARATING THE THREE MAJOR TYPES OF BLOOD CELLS FROM A WHITE BLOOD CELL HISTOGRAM

[75] Inventors: Ricky A. Marshall, Allentown; David G. Harlow, Bethlehem, both of Pa.

[73] Assignee: Serono-Baker Diagnostics, Inc., Allentown, Pa.

[21] Appl. No.: 281,250

[22] Filed: Dec. 7, 1988

[51] Int. Cl.$^5$ .............................................. G06F 15/42
[52] U.S. Cl. .............................................. 364/413.08
[58] Field of Search ..................... 364/413.07, 413.08; 382/6; 377/6; 356/39

[56] References Cited

U.S. PATENT DOCUMENTS

| | | | |
|---|---|---|---|
| 4,485,175 | 11/1984 | Ledis et al. | 436/63 |
| 4,581,334 | 4/1986 | Kirchanski et al. | 435/29 |
| 4,596,035 | 6/1986 | Gershman et al. | 382/6 |
| 4,882,284 | 11/1989 | Kirchanski et al. | 436/63 |

FOREIGN PATENT DOCUMENTS

| | | |
|---|---|---|
| 022670 | 1/1981 | European Pat. Off. |
| 259834 | 3/1988 | European Pat. Off. |
| WO84/02777 | 7/1984 | PCT Int'l Appl. |

OTHER PUBLICATIONS

EPO Search Report for EPO Application No. 80302360.5.

Primary Examiner—Jerry Smith
Assistant Examiner—David Huntley
Attorney, Agent, or Firm—Parmelee, Bollinger & Bramblett

[57] ABSTRACT

A method of analyzing and separating the three major populations, namely, lymphocytes, monocytes and granulocytes of white blood cells from a composite histogram containing the various types of white blood cells is provided by identifying a mode (highest frequency of occurrence) of both the lymphocyte and granulocyte concentrations by determining the highest sum of such populations over first predetermined ranges in the histogram. This is accomplished by determining the lymph and gran peaks along with 60% thresholds from said peaks and estimating the lymph and gran areas in providing a reconstituted lymph and gran curve. Lymph and gran population curves are then subtracted from the histogram resulting in a mid population curve whose peak is determined and from which is derived left and right thresholds based on the mid population peak. The left and right thresholds are then applied to the histogram and the areas to the left, between, and to the right of the thresholds are integrated in order to derive the lymph, mono and gran areas of the histogram. The method in effect provides discrima-. tors with moving thresholds which vary in accordance with changes in the histogram which compensate for changes in the temperature or lyse concentrations which affect the size distribution of the various white blood cell constituents.

10 Claims, 9 Drawing Sheets

INTEGRATION OF THESE CHANNELS REPRESENTS HEIGHT OF CHANNEL 65

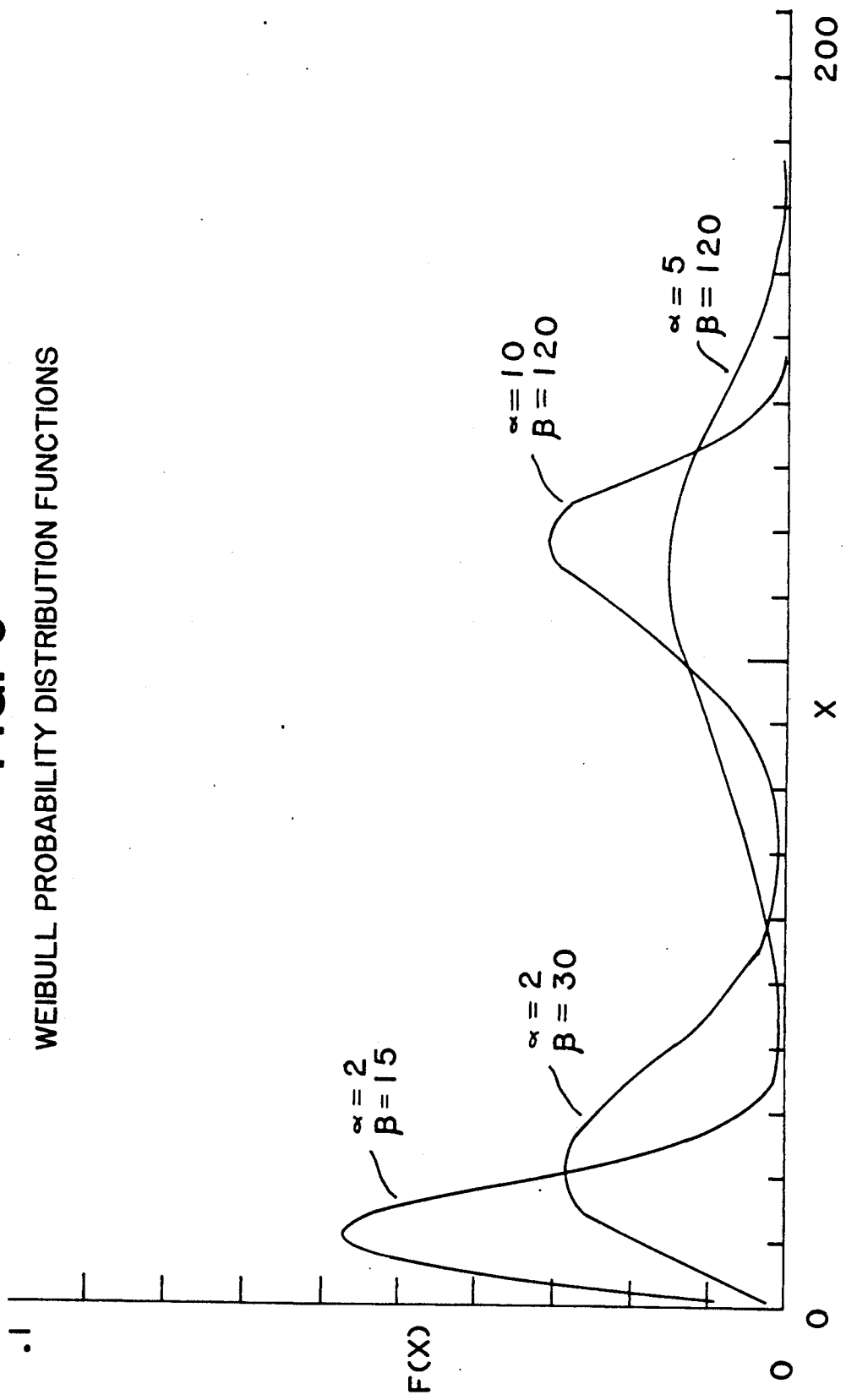

METHOD OF SEPARATING THE THREE MAJOR TYPES OF BLOOD CELLS FROM A WHITE BLOOD CELL HISTOGRAM

BACKGROUND OF THE INVENTION

This invention relates to the method of separating the three major populations of leukocytes, namely, lymphocytes (lymph), monocytes (mono), and granulocytes (gran) populations of white blood cells from a white blood cell histogram which has been derived from automated cell counters which electronically count and size cells employing the well known impedance principles.

To differentiate and identify white cell types, the white blood cells are differentially lysed into separate size classes. The size of each cell is then plotted against a frequency of occurrence into a composite histogram. This histogram contains all the types of white blood cells as is illustrated, for example, in U.S. Pat. No. 4,485,175. The histogram is then analyzed to separate out the three major types of white blood cells, namely, lymph, mono and gran populations of the white blood cells.

A number of difficulties have been involved in separating the three populations from the composite histogram which include the fact that the middle population can be extremely close to the left or lymph population of the histogram and sometimes a minimum point between these two populations cannot be found. The middle population of the histogram is also relatively small compared to the two surrounding populations constituting from 5 to 10% of the total histogram. The right gran population is extremely broad causing it to interfere with the mid population and the shape of the histogram, between the middle population and the gran population, is flat making it difficult to establish a stable minimum point therebetween. The gran population can also skew both left or right which makes the use of a log-normal curve fit very difficult. In addition, each population can vary in area from zero and normal curve fits tend to blow up for very small areas.

In the past, fixed discriminators have been provided setting thresholds levels between the three major populations. The counts are made using a large number of count channels which are divided by the discriminators having fixed threshold positions which do not change once they are set. Once the threshold positions are set an entire series of histograms is fed thereto. The nature of the middle population simply does not lend itself to the use of fixed discriminators which tend to miss the middle populations in any type of controls applied thereto. In addition, changes in temperatures or lyse concentrations affect the size distribution and by varying these parameters the location or width of each population will change. Therefore, in evaluating a histogram with discriminators having fixed thresholds, much thresholds will not factor in the varying parameters and will provide inaccurate counts.

The present invention is directed to overcome the aforesaid difficulties.

SUMMARY OF THE INVENTION

Accordingly, it is an object of this invention to provide a new and improved method of separating the three major populations of white blood cells of a white blood cell histogram which is superior to previous methods used for this purpose.

Still another object of this invention is to provide a new and improved method of analyzing a histogram for providing a more accurate count of the three populations of white blood cells which takes into account the varying conditions affecting the size distribution of the white blood cells such as changes in temperature or lyse concentration involved when the histogram is made.

In carrying out this invention, in one illustrative embodiment thereof, a method of analyzing and separating the three major populations lymphocytes, monocytes and granulocytes of white blood cells from a composite histogram containing the various types of white blood cells is provided which comprises identifying the modes (highest frequency of occurrence) of both the lymph and gran populations by determining the highest sum of lymph and gran populations over first and second predetermined ranges in the histogram. The gran and lymph mode populations so determined are used to derive lymph and gran population fitted curves which are then subtracted from the histogram resulting in a mid population curve. A determination is made of the peak of the mid population curves which is used to derive left and right thresholds based on integrating left and right areas of the population peaks of the mid population curve. Using the left and right thresholds on the original histogram and integrating the areas of the histogram separated by the threshold discriminators provides an accurate means for delineating and counting the three major white blood cell concentrations.

BRIEF DESCRIPTION OF THE DRAWINGS

The invention, together with further aspects, objects, advantages and features of the present invention will be more clearly understood from the following description considered in connection with the accompanying drawings.

FIG. 6 is a plot of F(x) vs. X for various alphas and betas for Weibull (pdf).

DESCRIPTION OF THE PREFERRED EMBODIMENTS

The present invention is directed to analyzing white blood cells in a blood sample. In order to differentiate between the white blood cells types which include three principle populations, namely, lymphocytes, monocytes (middle population) and granulocytes, the white blood cells in the sample are differentially lysed into separate size classes. The size of each cell is then plotted against the frequency of occurrence in a composite histogram, the graph which in one illustrative example contains approximately 255 channels. The histogram may be derived from the Baker System 9000 automated cell counter which electronically counts and sizes the cells employing the well known impedance principle. However, the present invention is not limited to this system and is applicable to all differentiating systems which produce the type of histogram used in the present invention. As has been pointed out, the invention is directed to differentiating between the three major groups of the white blood cells in which no clear delineation is normally provided by the histogram of a given sample. Prior approaches to the problem have utilized fixed discriminators to separate the three white blood cell types which discriminators are arbitrarily set between certain channels of the histogram. In accordance with the present invention, moving discriminators are provided which vary in position in accordance with the histogram produced from analyzing any given blood sample.

Figure 1:
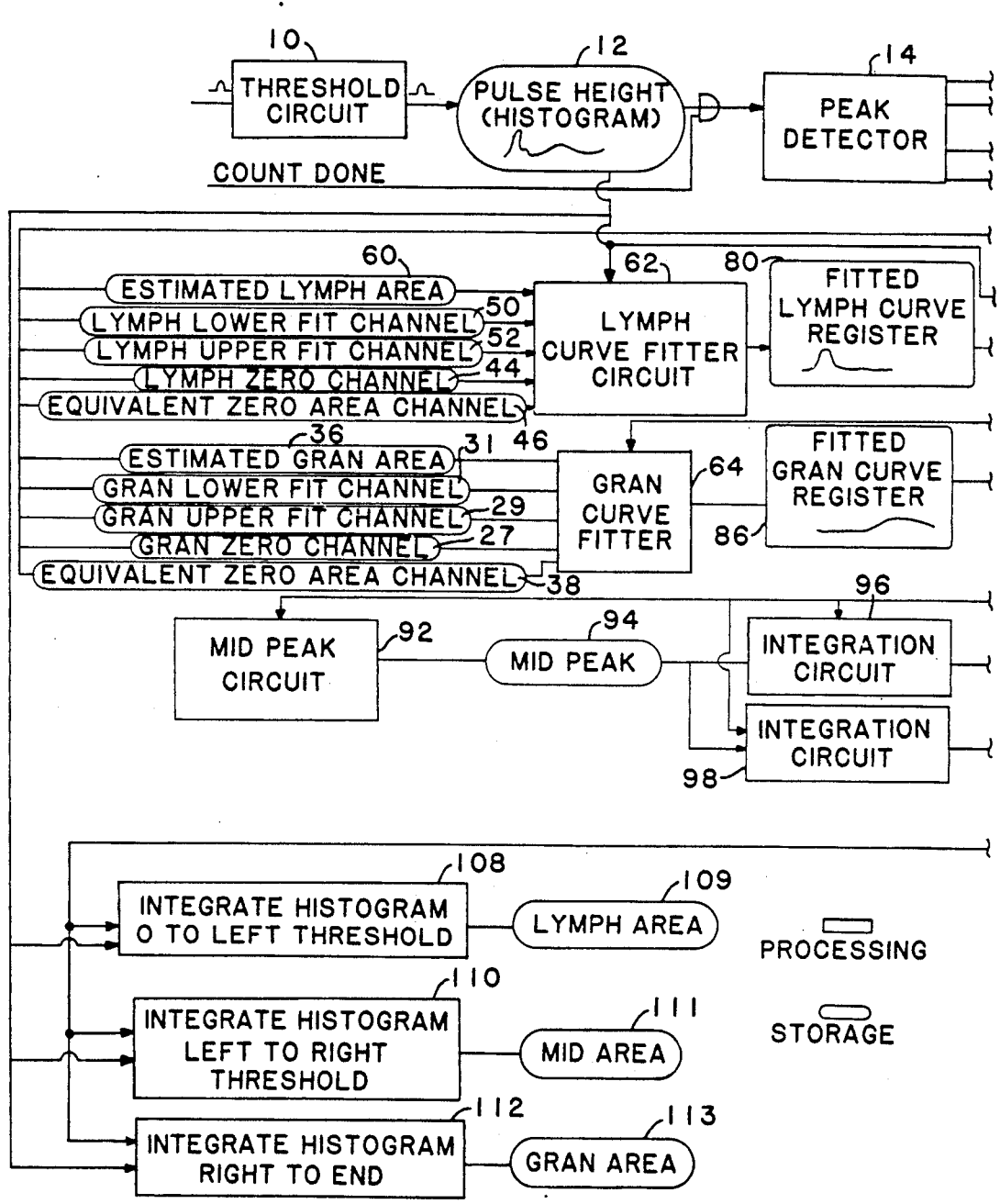
FIG. 1 is an electrical schematic block diagram of the method for separating the three major populations from a white blood cell histogram in accordance with the present invention.

Referring now to FIG. 1, a whole blood sample and a predetermined concentration of a diluent are mixed with a lysing reagent in a predetermined total volume which is applied to threshold circuitry 10 and stored in a pulse height memory 12 which provides the accumulated histogram from which the three major white blood cell populations will be determined. The threshold circuitry and pulse height memory may be provided by a Baker System 9000 automated cell counter or the like. The histogram from the pulse height memory 12 is applied, along with a while blood count done signal which merely delineates completed histograms for a given sample, to a peak detector 14. The purpose of the peak detector 14 is to characterize the lymph population which is done by finding the highest sum in one illustrative example of approximately seven channels over a given range in the histogram. The peak detector is also utilized to find the mode characteristic of the gran population which is done by finding the highest sum over another range of channels in which more channels are used, for example, 35 plus or minus a few channels which is a greater sum than used in the lymph population in order to compensate for greater variability in the gran population. The lymph population mode and the gran population mode are used to initially set discriminators for the lymph and gran mode which amounts to delineating the areas of the histogram occupied by the three major white blood cell populations. It will be appreciated that the selection of the number of channels used in peak detection are empirical values for a specific application. However, other values can be used depending on the data which is being processed.

Figures 1, 2:
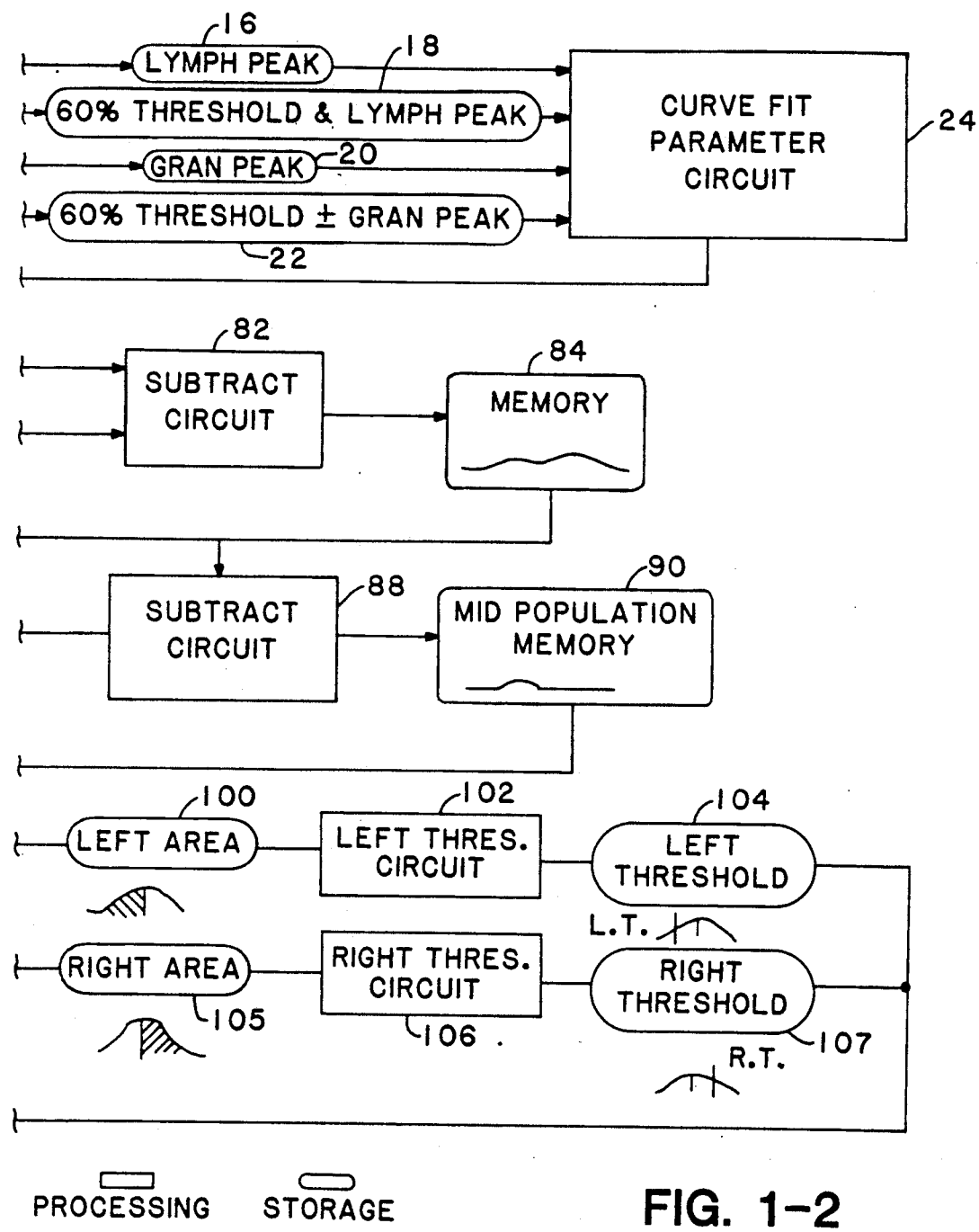
FIG. 2 is a graph of a group of channels of a portion of a histogram illustrating how the peak is selected by the peak detector in FIG. 1.
Figure 2:
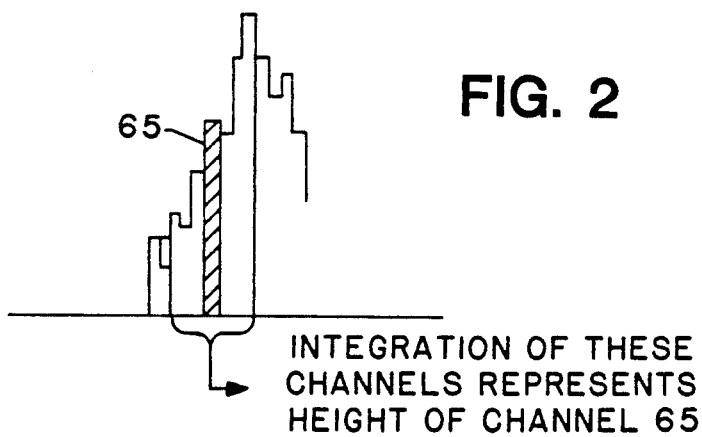
Figure 3:
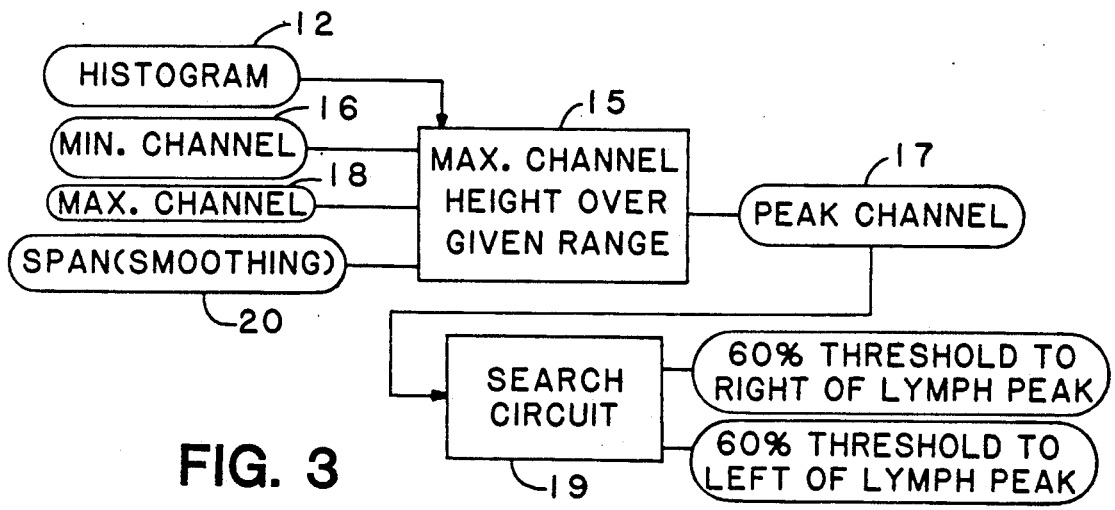
FIG. 3 is a schematic block diagram using the methodology illustrated in FIG. 2 for determining the channel with the highest value constituting the lymph or gran peak provided by the peak detector of FIG. 1.

FIGS. 2 and 3 illustrate the methodology used in obtaining the lymph and gran peaks from the peak detector 14. Since the data is noisy, a smoothing function is used. The height of a given channel in question is the sum of itself plus neighboring channels across a given span. As will be seen in FIG. 2, the height of an arbitrary channel on the histogram, for example, channel 65 which for purposes of illustration will be considered the channel with the highest value is arrived at from the summation of channel 65 plus or minus three contiguous channels. As will be seen in FIG. 3, the maximum channel height over a given range 15 has applied thereto the histogram 12, minimum channel data 16, maximum channel data 18 and a span smoothing function 20 in which the maximum channel height over a given range provides an output of the channel with the highest value to a peak channel register 17. The number of channels covered for finding the lymph peak covers a certain range in the histogram which is selected based on past knowledge of lymph populations and the same is true for the selection of channels for the gran population. It should be pointed out if the highest channel occurs at either the maximum channel or the minimum channel a peak is not given from the maximum channel height 15. The output of the peak channel register 17 is applied to a search circuit 19 which searches for the channel to the left and right of peak which falls below 60% of peak height and produces stored outputs in register 21 and 23.

Accordingly, the output of the peak detector 14 provides a lymph peak stored in register 16, a 60% threshold plus or minus the lymph peak is applied to a storage register 18, a gran peak 20 along with a 60% threshold plus or minus the gran peak are stored in a register 20 and 22, respectively, with the output of the registers 16, 18, 20 and 22 being applied to a curve fit parameter circuit 24. The 60% thresholds have been empirically chosen from a range of 30-90%. The function of the curve fit parameter circuit 24 is to estimate the areas of the three white blood cell populations by summing between the initial discriminators which have been set in accordance with the lymph and gran modes determined by the peak detector 14.

Figures 1, 4:
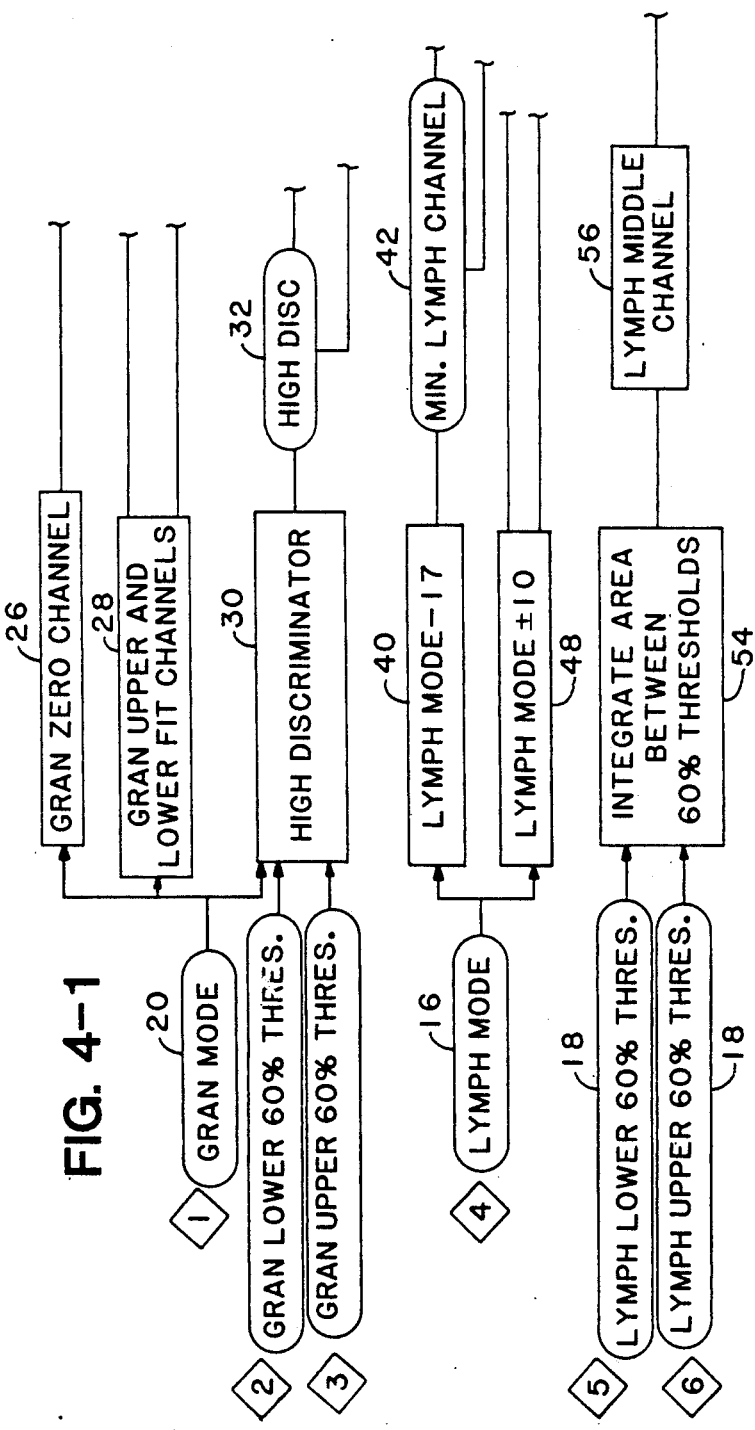
FIG. 4 is a block diagram illustration of the calculated parameters for the curve fit parameter circuit of FIG. 1.
Figure 5:
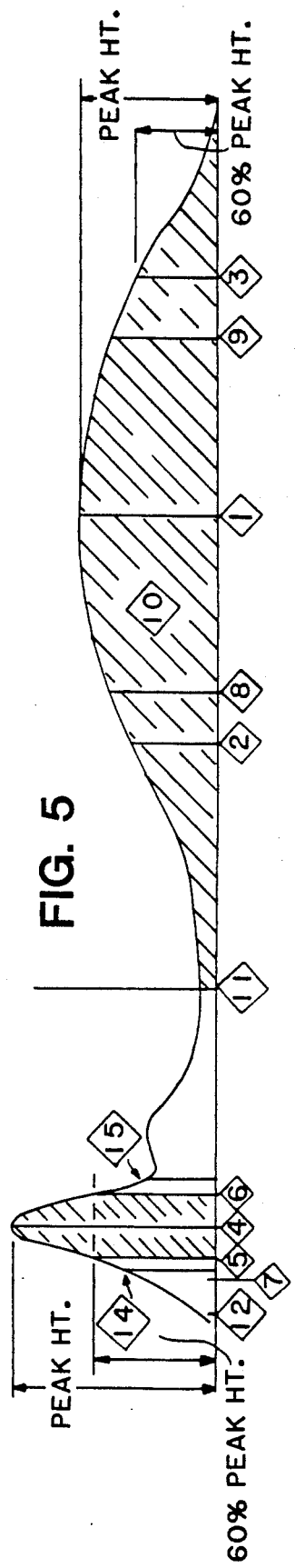
FIG. 5 is a curve of a histogram useful in explaining the operation of FIG. 4.
Figures 2, 4:
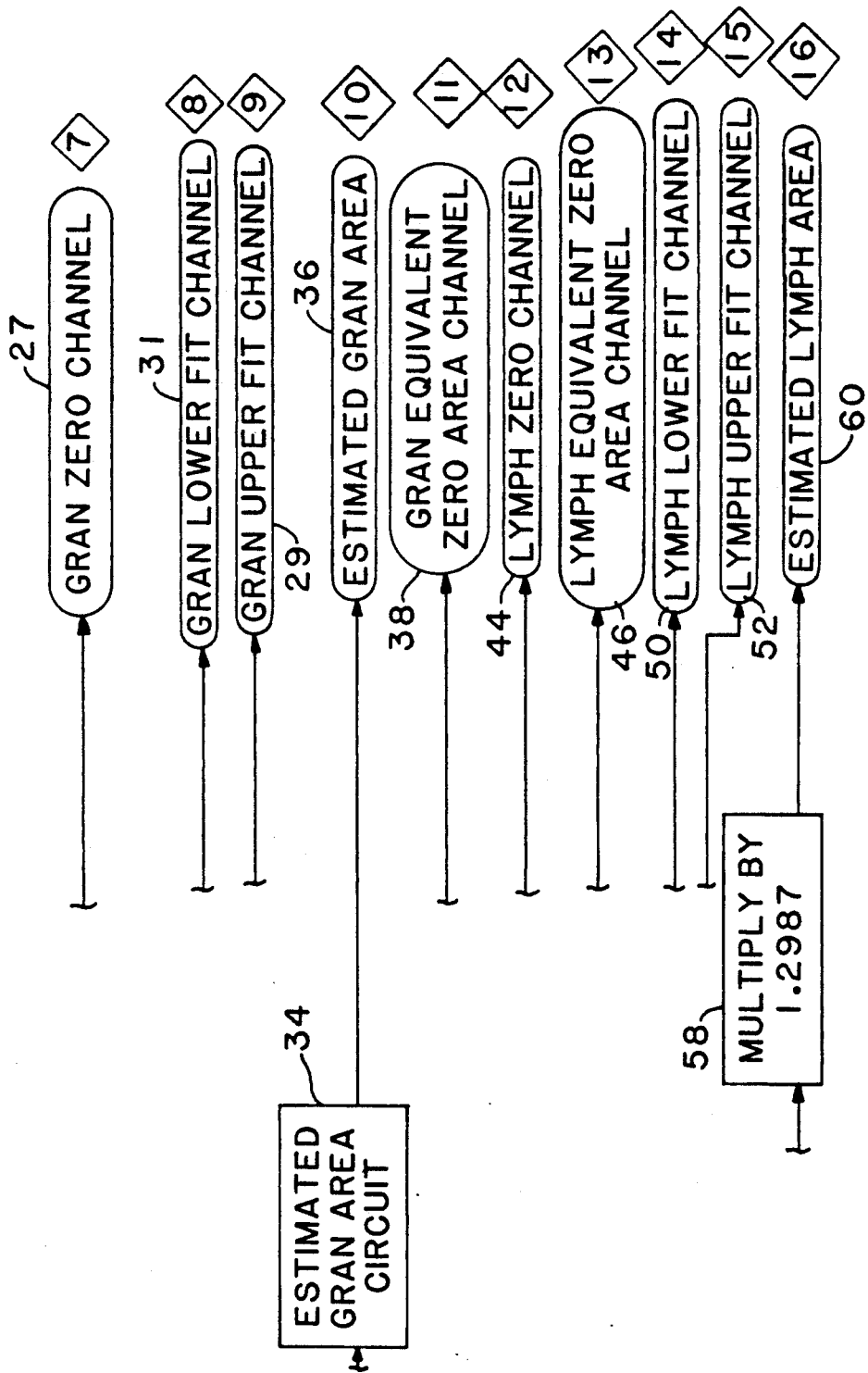

FIGS. 4 and 5 are used to explain the operation of the curve fit parameter circuit 24. The gran mode or peak of register 20 is applied to a gran zero channel circuit 26, to a gran upper and lower fit channel fit circuit 28, and to a high discriminator circuit 30. Gran upper and lower 60% thresholds are also applied to the high discriminator circuit 30. The gran zero channel is determined by using the gran peak minus [(gran mode minus gran lower threshold)$\times 3.7$)]$+15$ while the gran upper and lower fit channels are determined by using the gran mode plus or minus 50 channels. The high discriminator 30 is set by the gran mode minus (gran mode$-$gran low threshold) minus (gran upper threshold$-$gran mode). These equations are empirically derived and are based on the peaks and widths of the populations which are used to define input parameters. The output from the high discriminator circuit 30 is stored in the high discriminator register 32 and applied therefrom to an estimated gran area circuit 34 which integrates the area between the high discriminator and the right end of the histogram to provide a value which is stored in a register of the estimated gran area 36. The output of the high discriminator register 32 is also applied to a gran equivalent zero area channel register 38. The gran zero channel 26 is stored in a gran zero channel register 27 and the gran upper and lower fit channels 28 are stored in gran upper and lower fit channel registers 29 and 31, respectively. In order to better understand the operation of the curve fit parameter circuit 24 as explained in connection with the description of FIG. 4, diamond enclosed numerals have been placed next to the registers in the diagram in FIG. 4 and have been indicated on an illustrative histogram shown in FIG. 5 which is being analyzed in accordance with the methodology of the present invention.

Returning now to FIG. 4 to the lymph curve fit circuit 62 of FIG. 1, the lymph mode or peak 16 is applied to a lymph mode minus 17 (empirical value for this specific example) circuit 40 whose output is applied to a minimum lymph channel register 42 providing a lymph zero channel output to register 44 and a lymph equivalent zero area channel output to register 46. The lymph mode 16 is also applied to a lymph mode plus or minus 10 (empirical value for this specific example) circuit 48 which applies an output to lymph lower fit channel register 50 and a lymph upper fit channel register 52. The lymph lower and upper 60% threshold register outputs 18 are applied to an integrated area circuit 54 which integrates the area between the upper and lower 60% thresholds of the lymph populations of the histogram and applies the area to a lymph mode middle area circuit 56 which is applied to a multiplier circuit which multiplies the lymph middle area by 1.2987 (empirical value for this specific example) to provide an estimated lymph area to the register 60. Diamond enclosed numerals are show on FIG. 4 and FIG. 5 to illustrate the relationship of the derived parameters in FIG. 4 to the histogram in FIG. 5.

The curve fit parameter circuit 24 providing the parameters 60, 50, 52, 44 and 46 which are the lymph parameters, are provided and applied to a lymph curve fitter circuit 62 along with the histogram from the pulse height memory circuit 12. Likewise, the gran parameters from the curve fit parameter circuit 24, namely, registers 36, 31, 29, 27 and 38, are applied to a gran curve fitter circuit 64.

The purpose of the lymph curve fitter and the gran curve fitters 62 and 64, respectively, are to fit the lymph and gran populations to a Weibull probability distribution function. In the case of the lymph population this is done by transforming the cumulative distribution of the lymph population into a straight line and fitting the least squares line and calculating the Weibull parameters $\alpha$ and $\beta$ from the slope and intercept of the line. With respect to the gran population some of the parameters in the fit are determined by estimating the width of the distribution which is done by finding the channels to the right and left of the histogram which are at a given percentage of the height of the gran mode and corresponds to the 60% threshold values found by the peak detector circuit 14 in the example illustrated.

In order to better understand the purpose of the Weibull curve fit, an explanation is provided. There are several advantages to using the Weibull Probability Distribution Function (pdf) to fit the raw data of both the Lymph and Gran populations. The function has only two parameters (alpha and beta) which define its shape and location. By varying alpha and beta a wide variety of distributional shapes can be obtained. Unlike the Log-Normal equation, Weibull pdf is able to skew both to the left and to the right. This is especially important when fitting the Gran population.

The Weibull pdf is defined as:

$$F(x) = (alpha/beta) * (x/beta)^{(alpha-1)} * e^{-(x/beta)^{alpha}} \quad \text{(Eqn. 1)}$$

A plot of F(x) vs. x for various alphas and betas is shown in FIG. 6.

The cumulative distribution (cdf) is the integration of the pdf. It can be derived from the pdf and is as follows:

$$G(x) = 1 - e^{-(x/beta)^{alpha}} \quad \text{(Eqn. 2)}$$

Figure 7:
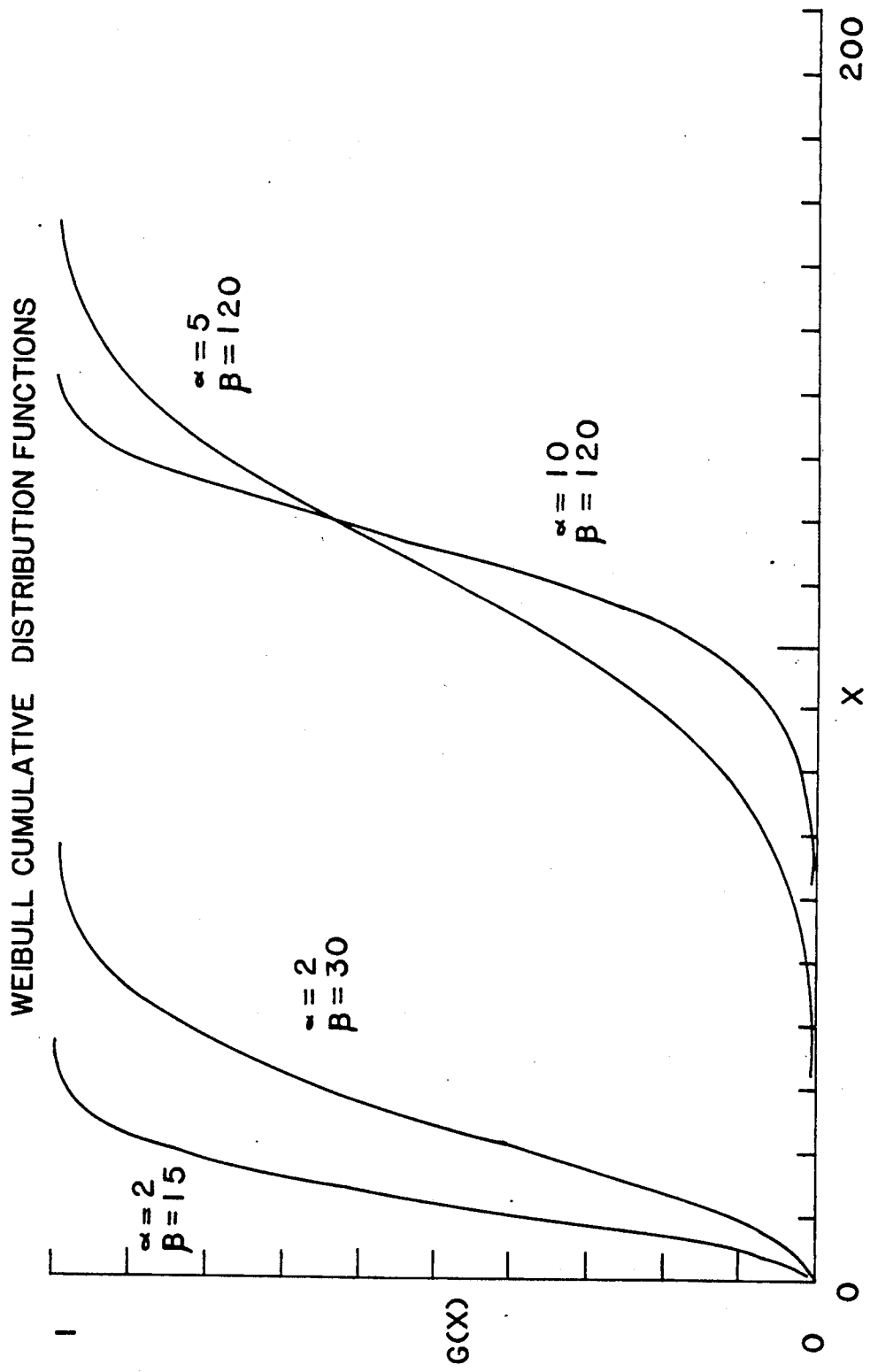
FIG. 7 is a plot of G(x) vs. X for various alphas and betas for Weibull (cdf).

Thus, G(x) is the summation of channels up to channel x. A plot of G(x) vs. x for various alphas and betas is shown in FIG. 7.

Equation 2 can also be rewritten as:

$$Ln[-Ln(1-G(x))] = alpha*Ln(x) - alpha*Ln(beta) \quad \text{(Eqn. 3)}$$

If we define:

$$Z(x) = Ln[-Ln(1-G(x))] \text{ and} \quad \text{(Eqn. 4)}$$

$$W(x) = Ln(x) \quad \text{(Eqn. 5)}$$

then equation 3 becomes:

$$Z(x) = alpha*W(x) - alpha*Ln(beta) \quad \text{(Eqn. 6)}$$

A straight line is obtained by graphing Z(x) vs. W(x) with a slope of alpha and an intercept of −alpha*Ln(beta).

To fit raw data to a Weibull pdf:
1) Calculate G(x) for every x (which is again, the summation of the channels up to x).
2) Calculate Z(x) for every x from G(x) using equation 4.
3) Calculate W(x) for every x from using equation 5.
4) Calculating the Least squares best fit line for G(x) vs. W(x). This will result in the slope and intercept.
5) Calculate alpha and beta from the slope and intercept using equation 6.

Once alpha and beta are found, a smooth, Weibull pdf curve can be constructed using equation 1. Since the area under a Weibull pdf is 1, the Weibull pdf must then be scaled using the estimated area of the population.

There are additional considerations when trying to fit real data. First, the Gran population does not go to zero before merging into the mid population. Rather, the two populations overlap. Thus, it is necessary to start integrating from a point representing zero area. The area to the right of this point represents the entire area of the gran population. This estimated point is called the EQUIVALENT ZERO CHANNEL.

Second, the Weibull pdf starts from x=0. In reality, granulocytes and lymphocytes will only physically get so small. Therefore, there will be some point which, to the left, there are no more grans (or lymphs in the case of lymphs). This point is called the ZERO CHANNEL and defines where the fitted curve must go to zero. For each curve fit, the zero channel is used to offset the x axis. During the fit and reconstruction of the curve, x is defined as the real channel number minus the zero channel.

Third, the further from a population's mode one gets, the more uncertain one is as to the type of the particle. For example, if one gets too far to the left of the gran mode, the data does not represent the amount of grans, but instead it starts to represent the amount of mids. Thus, one does not want to fit over the entire range of the population, but only over a smaller range about the mode. To do this, one fits only the data between the LOWER FIT CHANNEL and the UPPER FIT CHANNEL.

To start fitting at the Lower Fit Channel, an area representing the area up to that point must be calculated. The integrated area up to the point of the Lower Fit Channel is called the BEGIN AREA and is calculated by summing from the Equivalent Zero Channel to the Lower Fit Channel.

Figure 8:
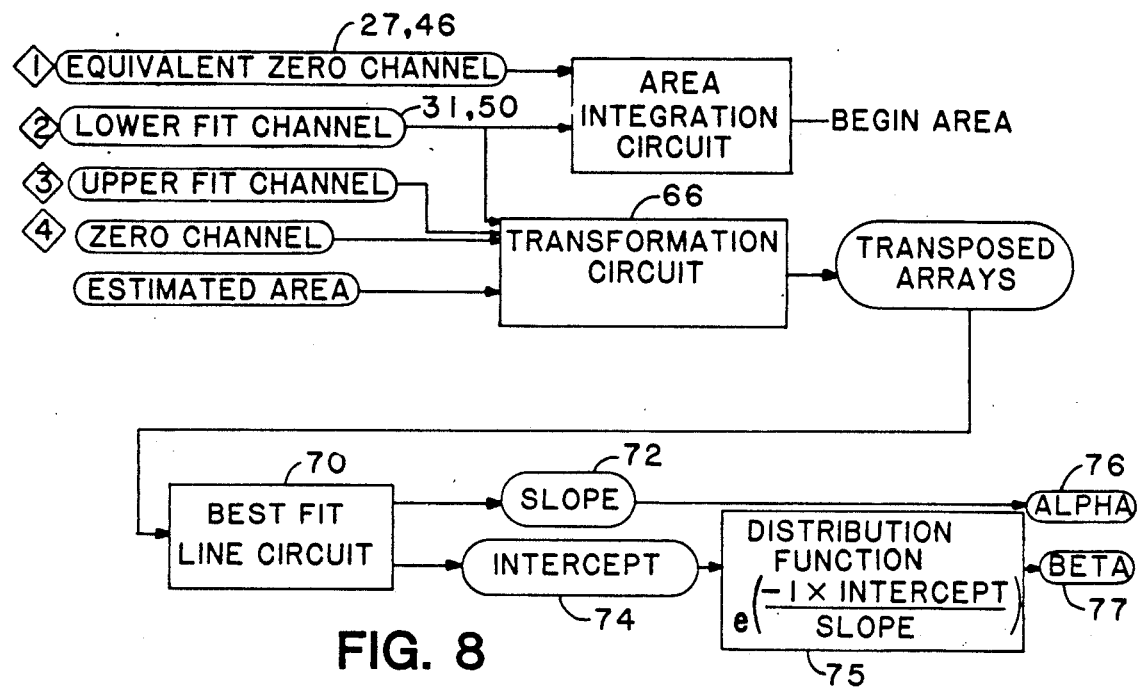
FIG. 8 is a curve fit block diagram used in explaining the operation of the lymph curve fitter and gran curve fitter circuits of FIG. 1.
Figure 9:
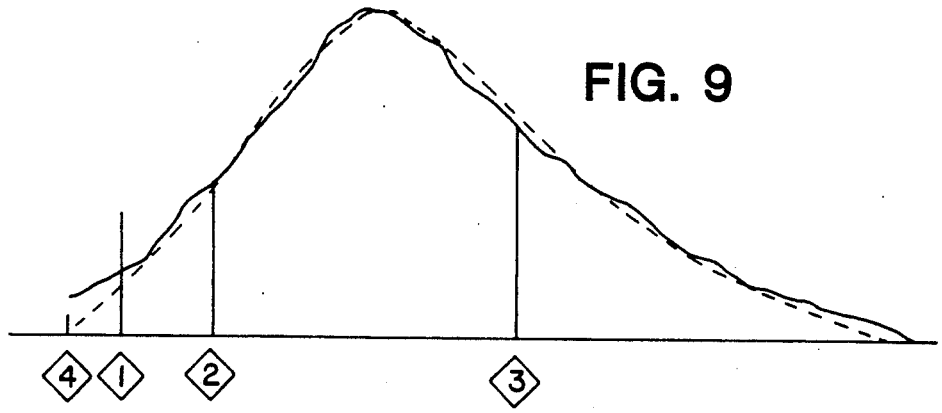
FIG. 9 is a curve useful in the explanation of the curve fitter block diagram of FIG. 6.

FIGS. 8 and 9 illustrate the functioning of the curve fitters 62 and 64. The curve fitter best fits data to the Weibull cumulative distribution function $$G(x) = 1 - e^{-\left(\frac{x}{\beta}\right)^\alpha},$$

(Eg. 2) where x is the transposed channel number by zero channel i.e. x=channel−zero channel where the solution to the fit is $\alpha$ and $\beta$. The purpose is the transformation of a curve to linear coordinates for both the lymph fit and the gran fit as is indicated on the histogram shown in FIG. 10. The lower fit channel, upper fit channel, zero channel and estimated area are applied to a transformation circuit 66. The output of the transformation circuit 66 is stored in a transposed array register 68 and applied to a best fit line circuit 70 using a least squares method in which the output is provided to a slope register 72 and an intercept register 74 with the slope of the line applied to the a register 76 and the intercept 74 applied to an equation circuit 75 representing $$e^{\left(\frac{-1 \times \text{intercept}}{\text{slope}}\right)}$$

providing the $\beta$ output 77. The reconstituted lymph curve fit is indicated in the dotted lines on FIG. 9.

Returning to FIG. 1, the output of the lymph curve fitter 62 is applied to the stored lymph curve register 80 which is applied to a subtract circuit 82 along with the histogram from the pulse height memory register 12 which subtracts the lymph curve fit from the histogram, the result which is stored in register 84 with the result being applied to gran curve fitter 64 producing a stored gran curve in register 86 which is applied to a subtract circuit 88 which in effect removes the fitted lymph and gran curves from the histogram producing an output of a mid population curve which is stored in the register 90. The mid population curve from register 90 is applied to a mid peak circuit 92 which scans for the mid peak in the mid population memory 90 producing a mid peak output stored in register 94. The output of the mid peak register 94 is applied to integration circuits 96 and 98 along with the output of the mid population register 90. Integration circuit 96 integrates the area to the left of the peak of the mid population while the integration circuit 98 integrates the area to the right of the peak producing outputs of the left area in register 100 and in the right area in register 101. The left area register 100 is applied to a left threshold circuit 102 which scans for the left threshold which is a percentage of the left area and provides a left threshold output to a left threshold register 104. The right area register 101 is applied to a right threshold circuit 106 which scans for the right threshold which is a percentage of the right area to produce a right threshold output to the right threshold register 107. The output of the left threshold register 104 and right threshold register 107 are applied to integration circuits 108, 110 and 112 along with histogram inputs from the pulse height register 12. The left and right thresholds represent the channels to the left and right of the mid population mode whose sum is a certain percentage of their areas. These channels thus provide the lower and upper discriminators 115 and 117 for the histograms. Integration circuit 108 integrates the histogram from the zero channel to the left threshold channel represented by the lower discriminator 115 illustrated in FIG. 10 to produce the lymph area 109. Accordingly, the percentage of lymph is the sum of the channels up to the lower discriminator 115 divided by the total area of the histogram. The integration circuit 110 integrates the histogram from the left or lower threshold 115 to the right threshold 117 supplying an output 111 to the mid area register 111 with the percentage of the middle population being the sum of the channels from the lower discriminator 115 to the upper discriminator 117 divided by the total area. The integrator 112 integrates the histogram from the right threshold to the right end of the histogram providing an output representing the gran area on storage register 113. The percentage of the grans is the sum of the channels from the upper discriminator 117 to the right end of the histogram.

Figure 10:
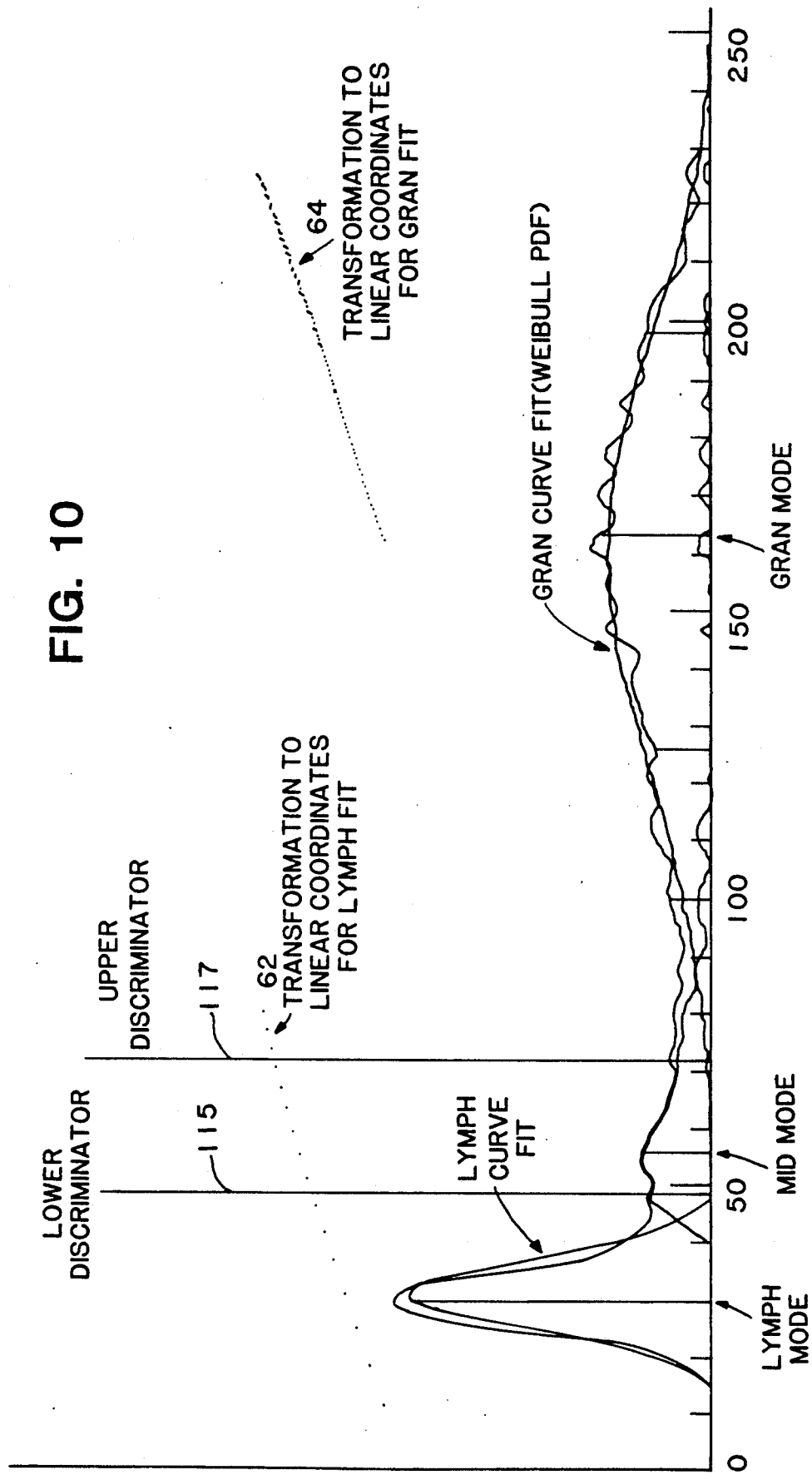
FIG. 10 shows a histogram illustrating the setting of the moving discriminators in accordance with the operation of FIG. 1.

Results of one illustration of the moving discriminators, namely, the lower and upper discriminators 115 and 117, respectively, are shown on the histogram in FIG. 10. The purpose, of course, is to be able to set the discriminators in accordance with the various changing shapes of the white blood cell populations. As the gran and lymph populations vary from sample to sample, as depicted in the associated histogram, the mid populations vary and are difficult to find. If the lower and upper discriminators, as shown in FIG. 10, are fixed and remain in the same place errors will be made as the populations shift from histogram to histogram. By providing moving discriminators using the methodology described, a more accurate reading is obtained for separating and delineating the three major populations provided by the histogram curves. The greater flexibility and accuracy provides better diagnosis of what is actually happening in the particular blood sample which is being analyzed.

Since other changes and modifications varied to fit particular operating requirements and environments will be apparent to those skilled in the art, the invention is not considered limited to the examples chosen for purposes of illustration, and includes all changes and modifications which do not constitute a departure from the true spirit and scope of this invention as claimed in the following claims and equivalents thereto.

What is claimed is:

1. A method of analyzing and separating the three major populations of white blood cells, lymphocytes, monocytes and granulocytes from a composite histogram derived from combining a whole blood sample and a predetermined concentration of a diluent mixed with a lysing reagent in a predetermined volume, and applying the predetermined volume to a cell counter including threshold circuitry and a pulse height memory comprising the steps of:

delineating a histogram containing lymph, mono, and gran populations from the pulse height memory of the cell counter for each whole blood sample.

predetermining a number of channels for the histogram delineated from the pulse height memory;

identifying a mode characteristic concentration of the lymph population by peak detecting and determining the highest sum of lymph population over a first predetermined number of channels in the histogram;

identifying a mode characteristic concentration of the gran population by peak detecting and determining the highest sum of gran population over a second different predetermined number of channels than the first predetermined number of channels and deriving lymph and gran population curves using lymph and gran curve fitter circuits and said gran and lymphy mode populations;

subtracting said lymph and gran population curves from said histogram for producing a mid population curve;

applying said mid population curve to a mid peak detector, storing the output of the mid peak detector and applying the stored mid peak output to integrating circuit means for identifying the mode characteristic concentration of said mid population curve;

deriving left and right thresholds based on integrating left and right areas of a mid population peak on said mid population curve;

applying said left and right thresholds to said histogram and integrating the areas of said histogram to the left of said left threshold, between the left and right thresholds and to the right of said right threshold using separate integrating circuit means for obtaining respectively, the lymph, mono and gran areas of said histogram for which the lymph, mono and gran counts are made.

2. The method as claimed in claim 1 wherein the step of identifying the mode characteristics of the gran population curve includes peak detecting the gran population along with upper and lower threshold levels of the peak, which peak is determined by obtaining the maximum channel height of the gran population over a given range which exclude either the minimum channel or the maximum channel of that given range.

3. The method as claimed in claim 1 wherein the step of identifying the mode of the lymph population includes peak detecting the lymph population along with upper and lower threshold levels of the peak, which peak is determined by obtaining the maximum channel height of the lymph population over a given range which excludes either the minimum or maximum channel of that given range.

4. The method as claimed in claim 3 wherein the step of identifying the mode characteristics of the gran population includes peak detecting the gran population along with upper and lower threshold levels of the peak, which peak is determined by obtaining the maximum channel height of the gran population over a given range which exclude either the minimum channel or the maximum channel of that given range.

5. The method as claimed in claim 4 wherein the step of deriving said lymph and gran population curves includes deriving curve fit parameters from the composite histogram for both the lymph and gran populations, the parameters being estimated areas, lower and upper fit channels, zero channels and equivalent zero channel which are utilized in forming the lymph and gran population curves.

6. The method as claimed in claim 5 wherein the step of deriving said lymph population curve includes the step of fitting the lymph population into the curve using a Weibull probability distribution function by transforming the cumulative distribution of the lymph population in the histogram into a straight line, estimating the distribution of population of the channels under the line and calculating Weibull parameters $\alpha$ and $\beta$ from the slopes and intercepts of the line on the histogram and forming therefrom a lymph fitted curve.

7. The method as claimed in claim 6 in which the subtracting step initially starts with the step of subtracting the lymph fitted curve from the original histogram.

8. The method as claimed in claim 7 wherein the step of deriving said gran population curve includes the step of fitting the gran population into a gran curve using a Weibull probability distribution function applied to the histogram and forming therefrom a gran fitted curve.

9. The method as claimed in claim 8 in which the step of subtracting said gran population curve occurs subsequent to said subtraction of said lymph fitted curve from said histogram and employs the gran fitted curve thereby providing said mid population curve.

10. The method as claimed in claim 9 wherein the step of making the lymph, mono and gran counts includes summing the area from a first end of the histogram to the left threshold, summing the area between the left and right thresholds and summing the area from the right threshold to a second end of the histogram, and dividing each summed area by the total area of the histogram.

* * * * *